US00PP26793P3

(12) United States Plant Patent
Bédard

(10) Patent No.: US PP26,793 P3
(45) Date of Patent: Jun. 7, 2016

(54) FLORIBUNDA ROSE PLANT NAMED 'WEKMAJUCHI'

(50) Latin Name: *Rosa hybrida*
Varietal Denomination: WEKmajuchi

(71) Applicant: Early Morning LLC, Pomona, CA (US)

(72) Inventor: Christian Bédard, Placentia, CA (US)

(73) Assignee: EARLY MORNING LLC, Pomona, CA (US)

( * ) Notice: Subject to any disclaimer, the term of this patent is extended or adjusted under 35 U.S.C. 154(b) by 86 days.

(21) Appl. No.: 14/121,988

(22) Filed: Nov. 12, 2014

(65) Prior Publication Data

US 2016/0135342 P1 May 12, 2016

(51) Int. Cl.
*A01H 5/02* (2006.01)

(52) U.S. Cl.
USPC ..... Plt./145

(58) Field of Classification Search
USPC ..... Plt./145
See application file for complete search history.

(56) References Cited

U.S. PATENT DOCUMENTS

PP17,175 P2 10/2006 Carruth
PP18,473 P2 2/2008 Carruth

*Primary Examiner* — Annette Para
(74) *Attorney, Agent, or Firm* — McKee, Voorhees & Sease, PLC

(57) ABSTRACT

A new variety of Floribunda rose suitable for garden decoration, having flowers of pure even gold yellow coloration.

1 Drawing Sheet

Classification: The present invention relates to a new *Rosa hybrida* plant.

Variety denomination: The new plant has the varietal denomination 'WEKmajuchi'.

BACKGROUND OF THE INVENTION

This invention relates to a new and distinct variety of Floribunda Rose. It has as its seed parent the variety known as 'WEKlezpat' (U.S. Plant Pat. No. 17,175) and as its pollen parent the variety known as 'WEKvossutono' (U.S. Plant Pat. No. 18,473).

SUMMARY OF THE INVENTION

Among the features which distinguish the new variety from other presently available and commercial rose cultivars known to the inventor are the following combinations of characteristics: its large flower size for the class, its strong fruity to moderately spicy fragrance, its excellent color stability throughout the life of the flower and its hairy peduncle and surface of the bud. The plant has a bushy upright growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKmajuchi' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKlezpat' by the following combination of characteristics: whereas 'WEKmajuchi' bears double flowers (about 26 to 42 petals) of pure even gold yellow coloration, 'WEKlezpat' bears very double flowers of butter gold blushed pink coloration with significantly heavier petalage (about 48 to 72 petals). The new variety is classified as a Floribunda rose with a bushy upright growing habit (about 120 to about 160 cm. spread at the widest point), whereas the seed parent is classified as an Hybrid Tea rose with a significantly more upright and less spreading growing habit (about 62 to about 90 cm. spread at the widest point).

The new variety may be distinguished from its pollen parent, 'WEKvossutono' by the following combination of characteristics: whereas 'WEKmajuchi' bears flowers with a strong fruity to moderately spicy fragrance, 'WEKvossutono' bears flowers with a strong licorice fragrance. The new variety has a bushy upright growing habit (about 120 to about 160 cm. in height and about 120 to about 160 cm. spread at the widest point), whereas the pollen parent has a compact and bushy significantly shorter and more compact growing habit (about 70 to about 85 cm. in height and about 50 to about 65 cm. spread at the widest point).

COMPARISON WITH THE CLOSEST COMMERCIALLY AVAILABLE CULTIVAR

The closest commercially available cultivar to the new variety is the pollen parent 'WEKvossutono' (U.S. Plant Pat. No. 18,473).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, Calif. in the month of October. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, Calif. in the month of October. Phenotypic expression may vary with environmental, cultural and climatic conditions, as well as differences in conditions of light and soil.

FLOWER

The new variety usually bears its flowers in clusters of two to five per stem. Flowers are borne in regular rounded clusters on strong moderately short stems (about 13 to about 32 cm.). Outdoors, the plant blooms abundantly and nearly continuously during the growing season. The flowers have a strong fruity to moderately spicy fragrance.

BUD

The peduncle is about 4.6 to about 8.2 cm. in length, of somewhat heavy caliper (about 0.2 to about 0.4 cm. in diameter), and usually erect. It is smooth with many hairs. Peduncle color is between 146B and 146A sometimes lightly suffused, especially on the side exposed to the sun, with between 187B and 187A.

Before the calyx breaks, the bud is about 1.2 to about 1.8 cm. in diameter at the widest point, about 2.0 to about 2.6 cm. in length, and pointed to somewhat ovoid in shape with a conspicuous neck. The surface of the bud bears between 2 to 8 foliaceous appendages with some hairs, usually with slender entire foliaceous parts extending beyond the tip of the bud about ¼ or more of its length. Bud color is between 137C and 146A sometimes lightly suffused, especially on the side exposed to the sun, with between 187B and 187A.

The sepals are about 1.9 to about 2.7 cm. in length and about 0.8 to about 1.2 cm. in width at the widest point. The outer surface color of the sepal is between 137C and 146A sometimes lightly suffused, especially on the side exposed to the sun, with between 187B and 187A. The outer surface of the sepal is smooth and bears between 0 to 4 foliaceous appendages with some hairs. The inner surface color of the sepal is near 146B broadly bordered by near 137A. The inner surface of the sepal is covered with fine wooly tomentum; sepal margins are lined with few stipitate glands and many hairs.

The receptacle of the flower is moderately long in length (about 0.5 to about 1.1 cm.) and somewhat heavy in caliper (about 0.6 to about 1.2 cm. in diameter). The receptacle is urn-shaped in form. Its surface is smooth with few hairs and with thick fleshy walls. The receptacle color is between 144A and 146A.

As the petals open (after the calyx breaks), the bud is about 1.8 to about 2.6 cm. in diameter at the widest point, about 2.6 to about 3.4 cm. in length, and moderately ovoid to somewhat pointed in form. The color of the under surfaces of the newly opened petals is between 15B and 16B. There is no visible change in coloration at the point where the petal attaches. The color of the upper surfaces of the newly opened petals is between 13A and 14B. There is no visible change in coloration at the point where the petal attaches.

BLOOM

When fully open, the bloom ranges from about 8.2 to about 11.0 cm. in diameter. Petalage is double with about 26 to 42 petals and about 5 to 9 petaloids irregularly arranged. When partially open, the bloom form is cupped to somewhat high centered, and the petals are moderately tightly spiraled to somewhat cupped and slightly undulated with petal edges slightly reflexed outward. When fully open, the bloom form is moderately cupped, and the petals are loosely cupped to undulated with petal edges moderately reflexed to somewhat rolled outward.

PETALS

The substance of the petals is heavy and of moderately thick thickness, with upper surfaces somewhat satiny and under surfaces slightly shiny. The petals are about 2.7 to about 4.5 cm. in length and about 2.4 to about 4.8 cm. in width at the widest point. Petal margins are entire.

The outer petals are nearly rounded to somewhat obovate in shape with rounded apices to sometimes slightly mucronate.

The inner petals are nearly rounded to somewhat obovate in shape with rounded apices to sometimes slightly mucronate.

Petaloids are about 0.9 to about 3.2 cm. in length and about 0.6 to about 3.0 cm. in width at the widest point. Petaloids are irregularly shaped moderately oblanceolate to somewhat subulate with rounded apices.

NEWLY OPENED FLOWER

The under and upper surface color of the outer petals is between 11B and 16C. There is no visible change in coloration at the point where the petal attaches.

The under and upper surface color of the intermediate and inner petals is between 10B and 17D.

The under and upper surface colors of the petaloids are similar in coloration to the upper and under surfaces of the intermediate and inner petals.

The general tonality of the newly opened flower is between 10B and 17D.

THREE-DAY-OLD FLOWER

The under surface color of the outer, intermediate and inner petals is between 8C and 14D. There is no visible change in coloration at the point where the petal attaches. The upper surface color of the outer, intermediate and inner petals is between 10C and 14D. There is no visible change in coloration at the point where the petal attaches.

The under and upper surface colors of the petaloids are similar in coloration to the upper and under surfaces of the intermediate and inner petals.

The general tonality of the three-day-old flower is between 10C and 14D.

On the spent bloom, the petals usually drop off cleanly.

In October in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 135) and are arranged regularly about the pistils; a few are mixed with petaloids or tucked in the calyx. The filaments are of irregular length (about 0.5 to about 1.3 cm.) most with anthers. Filaments are between 12A and 12B in color sometimes lightly suffused with between 53B and 53C. The anthers are of medium size for the class and all open approximately at the same time. Anther color when immature is near 23B on the external part and near 13D on the internal part. Anther color at maturity is near 164C on the external part and near 200A on the internal part. Pollen is abundant and between 18B and 16D in color.

FEMALE REPRODUCTIVE ORGANS

Pistils vary in number (average about 110). The styles are moderately uneven, somewhat short in length (about 0.3 to about 0.8 cm.), average in caliper, and loosely bunched to moderately separated. Stigma color is near 16C. Style color is between 145C and 145D often heavily suffused near the top with between 53A and 60A. Ovaries are usually all enclosed in the calyx.

Hips are moderately long in length (about 1.0 to about 2.5 cm.), rounded in form, and between 30C and 28A in color when ripe. The hip surface is smooth and with thick fleshy walls. The sepals are moderately permanent and usually straight in shape.

The seeds are irregularly rounded, smooth in texture, approximately 12 to about 23 per hip, about 0.5 to about 0.7 cm. in diameter at the widest point and between 164C and 165C in color.

FOLIAGE

The compound leaves are usually comprised of three to seven leaflets and are borne abundantly. The five-leaflet leaves are about 8.8 to about 15.8 cm. in length and about 7.8 to about 11.3 cm. in width at the widest point, moderately leathery to somewhat crisp in texture, and moderately glossy in finish on the upper side and matte to slightly glossy in finish on the under side. The leaves have a pinnate venation pattern. The terminal leaflets are about 4.4 to about 7.6 cm. in length and about 3.5 to about 5.4 cm. in width at the widest point, shaped ovate with acute to somewhat acuminate apices and rounded bases. Their margins are usually simply serrate.

The upper surface color of the mature leaf is between 139A and 147A. The under surface color of the mature leaf is between 147B and 146B. The under and upper colors of the leaf veins on the mature leaf are similar in coloration to the upper and under surfaces colors of the mature leaf The upper surface color of the young leaf is between 137A and 146A, often moderately suffused with between 187A and 187B. The under surface color of the young leaf is between 138B and 139C, often moderately suffused with between 187B and 187A. The under and upper colors of the leaf veins on the young leaf are similar in coloration to the upper and under surfaces colors of the young leaf.

The rachis is average in caliper and rough. The upper side is shallowly grooved with some hairs and few stipitate glands on the edges of the grooves. The under side of the rachis is rough with few hairs and stipitate glands and few small prickles. The rachis color is near 146C on the under side and near 137C on the upper side.

The stipules are about 1.0 to about 1.4 cm. in length and of medium width (about 0.5 to about 0.6 cm.) with moderately short straight points that usually turn out at an angle of more than 45 degrees and sometimes recurve toward the stem. The under and upper surface color of the stipule is between 146B and 138A.

The petiole is average in caliper and rough. The upper side is shallowly grooved with some hairs and few stipitate glands on the edges of the grooves. The under side of the petiole is rough with few hairs and stipitate glands and few small prickles. The petiole is about 1.6 to about 2.4 cm. in length and about 0.1 to about 0.15 cm in width at the widest point. The petiole color is near 146C on the under side and near 137C on the upper side.

The plant displays an average degree of resistance to powdery mildew and rust as compared to other commercial varieties grown under comparable conditions in Wasco, Calif. The plant's winter hardiness and drought/heat tolerance are yet to be determined.

GROWTH

The plant has a bushy upright medium height growing habit (about 120 to about 160 cm. in height and about 120 to about 160 cm. spread at the widest point), with full branching. It displays moderately vigorous growth and the canes are of medium to somewhat heavy caliper for the class (about 2.3 to about 3.0 cm. in diameter at the widest point).

The color of the major stems is between 146A and 146B. They bear many large prickles that are about 0.8 to about 1.1 cm. in length. The large prickles are almost straight to angled slightly downward with a moderately short somewhat broad oval base; prickle color is near 199A often heavily suffused with 201B and 201C. The major stem bears few small prickles of similar shape and coloration.

The color of the branches is between 146A and 146B. They bear some large prickles which are of similar size and shape to the large prickles on the major stems; prickle color is between 146C and 152D sometimes lightly suffused with near 187D. The branches bear few small prickles of similar shape and coloration.

The color of the new shoots is between 146B and 146A sometimes moderately suffused with between 187B and 187A. They bear few large prickles which are of similar size and shape to the large prickles on the major stems; prickle color is between 146B and 137D often moderately suffused with between 187B and 187C. The shoots bear very few small prickles of similar shape and coloration.

I claim:

1. A new and distinct Floribunda rose plant of the variety substantially as described and illustrated herein.

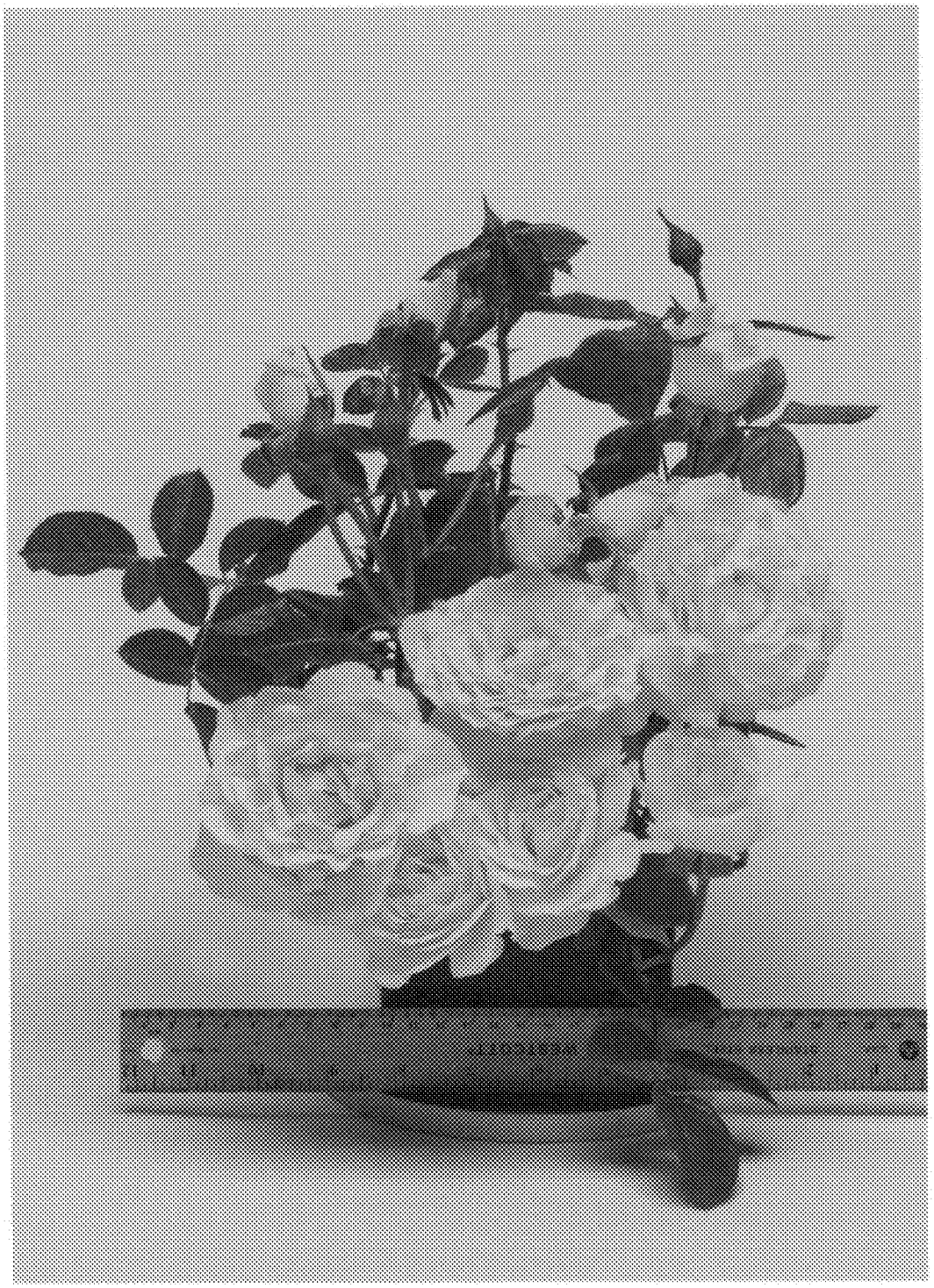

* * * * *